United States Patent
Srocka et al.

(10) Patent No.: US 8,837,807 B2
(45) Date of Patent: Sep. 16, 2014

(54) INSPECTION METHOD WITH COLOR CORRECTION

(75) Inventors: Bernd Srocka, Berlin (DE); Marko Doring, Dresden (DE)

(73) Assignee: HSEB Dresden GmbH, Dresden (DE)

( * ) Notice: Subject to any disclaimer, the term of this patent is extended or adjusted under 35 U.S.C. 154(b) by 322 days.

(21) Appl. No.: 13/289,536

(22) Filed: Nov. 4, 2011

(65) Prior Publication Data

US 2012/0114220 A1    May 10, 2012

(30) Foreign Application Priority Data

Nov. 5, 2010    (DE) .......................... 10 2010 060 375

(51) Int. Cl.
- *G06K 9/00* (2006.01)
- *G01N 21/95* (2006.01)
- *G06T 7/00* (2006.01)
- *G01N 21/956* (2006.01)

(52) U.S. Cl.
CPC ...... *G01N 21/95* (2013.01); *G06T 2207/20021* (2013.01); *G06T 2207/30148* (2013.01); *G06T 2207/10024* (2013.01); *G01N 21/9501* (2013.01); *G06T 7/001* (2013.01); *G01N 21/95607* (2013.01)
USPC ........... 382/145; 382/141; 382/147; 382/149; 382/274; 382/275

(58) Field of Classification Search
USPC ......... 382/100, 141–152, 254, 270–272, 274, 382/275
See application file for complete search history.

(56) References Cited

U.S. PATENT DOCUMENTS

| | | | |
|---|---|---|---|
| 4,644,172 A | 2/1987 | Sandland et al. | |
| 5,808,735 A * | 9/1998 | Lee et al. | 356/369 |
| 7,639,860 B2 * | 12/2009 | Sasai | 382/141 |
| 7,646,908 B2 * | 1/2010 | Onishi | 382/154 |
| 8,498,489 B2 * | 7/2013 | Abe et al. | 382/209 |
| 2005/0201622 A1 * | 9/2005 | Takarada | 382/218 |
| 2007/0177787 A1 * | 8/2007 | Maeda et al. | 382/141 |
| 2009/0226076 A1 * | 9/2009 | Sakai et al. | 382/149 |

FOREIGN PATENT DOCUMENTS

| | | |
|---|---|---|
| DE | 102004055250 | 5/2006 |
| DE | 102005036564 | 2/2007 |
| EP | 0927348 | 7/1999 |
| EP | 1213569 | 6/2002 |
| WO | WO00/04488 | 1/2000 |
| WO | WO 2009128505 A1 * | 10/2009 |

* cited by examiner

*Primary Examiner* — Eric Rush
(74) *Attorney, Agent, or Firm* — Thorpe North & Western LLP

(57) ABSTRACT

A Method for inspecting flat objects, especially wafers, with an object surface, comprises the steps of: scanning a digital image with a plurality of image points of said object surface with color- or grey values for each of said image points; detecting defects on said object surface by comparing said scanned digital image to a digital reference image; defining and selecting corresponding portions in said scanned digital image and in the digital reference image; determining a representative color- or grey value for each of said selected portions; calculating a compare value from said representative color- or grey value of said scanned digital image of a portion and a representative color- or grey value of said digital reference image of the same portion; and correcting each image point of said scanned digital image with a correction value determined from said compare value of step (e).

12 Claims, 2 Drawing Sheets

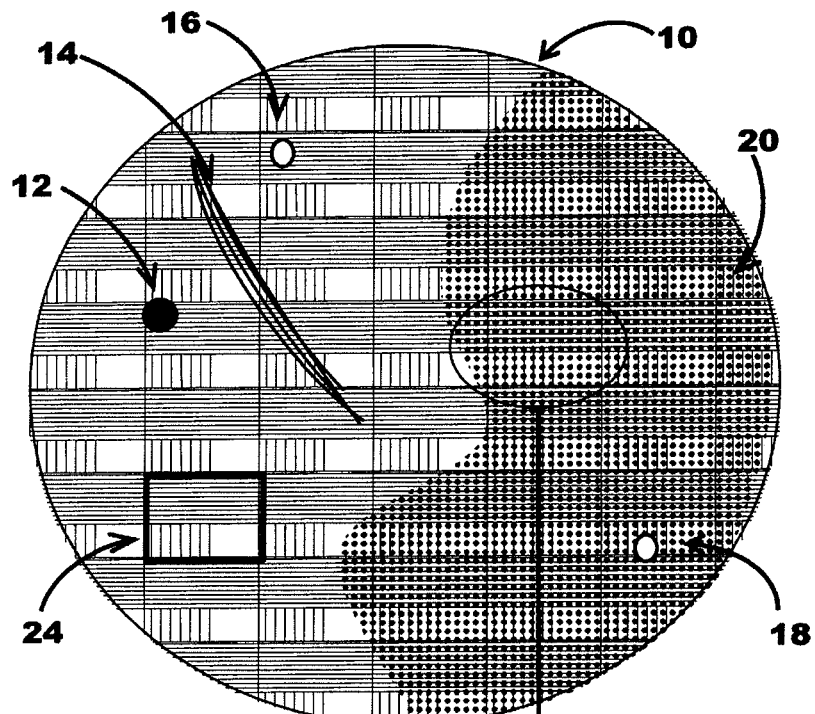
Fig. 1a
 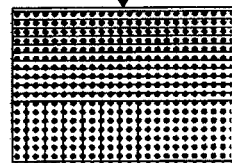 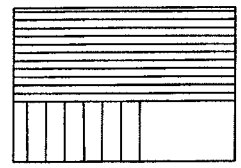
Fig. 1b　　Fig. 1c　　Fig. 1d

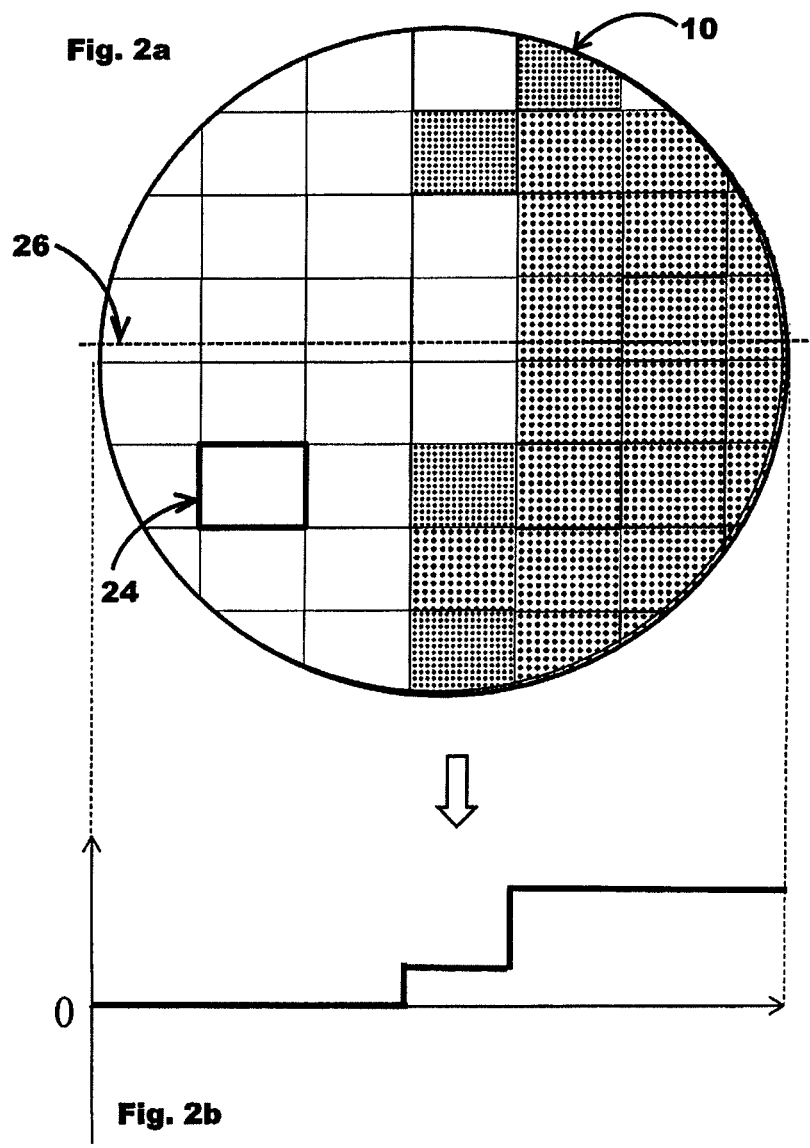

INSPECTION METHOD WITH COLOR CORRECTION

TECHNICAL FIELD

The invention relates to a method for inspecting flat objects, especially wafers, comprising the steps of:
  (a) scanning a digital image of the object surface with color- or grey values for each image point;
  (b) detecting defects on the object surface by comparing the scanned digital image to a digital reference image.

In different branches of the industry flat products are inspected for defects with imaging methods. In semiconductor- and solar cell industry these products are, amongst others, wafers. Wafers are discs of semiconductor-, glass-, sheet- or ceramic materials. The wafers are inspected entirely or at least with large portions thereof. Such an inspection is called Macro-inspection. The lateral resolution required for the detection of the interesting defects increases with developments of the general production technique. Typically, resolutions of 5 microns or less in macro-inspection are required for new technologies. At the same time, devices having a high throughput of wafers for inspection are desirable.

Further to the resolution the detection threshold is an important criteria. Often, defects vary only very little from their environment. It is then difficult to detect such defects. This relates to both small defects and large defects. Color variations may occur on the objects which are inspected, which are not considered to be a defect. Such color variations are often caused by the technology. They should be tolerated by the inspection systems.

Analogue tasks must be solved in different branches of the industry. Displays must be inspected for defects during their production in flat-panel industry. Imaging methods for the entire surface of the displays are used for the search of defects. In the electro industry defects on series of objects are determined with optical methods during the inspection of circuit boards.

It is a need common for all such applications to have a quick inspection for a high amount of objects which are usually of the same kind. Such objects are circuit boards, wafers, solar cells, displays and the like. All applications also use sensors for the generation of a large image of the objects. The images can be generated with optical imaging systems or with point-wise operating systems, depending on the kind of the defects searched for. Optical imaging systems are, for example, array- or line cameras. Point-wise operating sensors are, for example, detectors for measuring the reflection of optical rays, microwaves or acoustic waves. Also, magnetic sensors may be used.

PRIOR ART

Usually a plurality of wafers of the same kind or other objects are inspected. For this case, known methods use a particularly good wafer as a reference object which preferably has no defects. The defect-free wafer provides the "golden image" as a reference. However, it is also possible to generate such a reference image in a different way, such as, for example, with mathematical methods by using repeating structures on one wafer or by using several wafers.

WO 00/04488 (Rudolph) discloses a method for the generation of a reference image by optically observing a plurality of known, good quality wafers. Unknown wafers are inspected using a model which operates with this reference image.

U.S. Pat. No. 4,644,172 (Sandland) discloses an inspection method where a reference image is manually selected and stored during a training. The inspection is carried out in pre-selected geometries and compared to the stored reference image. Average values and standard variations are calculated with this method.

Real surfaces have production variations which may occur in the form of color variations.

DISCLOSURE OF THE INVENTION

It is an object of the invention to provide a method of the above mentioned kind with an improved recognition of defects. According to one aspect of the invention, this object is achieved with a method which is characterized by the steps of:
  (c) selecting corresponding portions in the scanned digital image and in the reference image;
  (d) determining a representative color- or grey value for each of the selected portions;
  (e) calculating a compare value from the representative color- or grey value of the scanned digital image of a portion and the representative color- or grey value of the reference image of the same portion; and
  (f) correcting each image point of the scanned digital image with a correction value determined from the compare value of step (e).

In this method the reference image may be generated with mathematical methods. In particular, such a mathematically generated reference image can be a compare image or a portion deduced from the environment of the image under inspection.

It is irrelevant for the subject matter of the invention if the scanned digital image is technically composed of image portions which are individually processed or if the scanned digital image is assembled to an image of the object which is then processed as a whole. Without limiting the general idea it is therefore referred to an image representative for all scanned digital images or portions of images.

Each of the images of an object is scanned and described with one or more color channels. If only one color channel is selected, a value is attributed to each image point of the image indicating the grey value, i.e., one of for example, 256 brightness values. This is a black and white image. In a RGB-color space, the brightness values are indicated in the colors red, green and blue. The image is composed of three brightness values per image point. It is also possible to use different color spaces for the description of the image, such as, for example, CMYK-color space.

The representative color- or grey value may be, in particular, the arithmetic average value or the median value of the color- or grey values for the image points in the selected portion.

With the present invention the scanned digital image and the reference image are divided into portions of a suitable size. Then a representative value, for example an average color- or grey value, for each color channel is determined for the scanned digital image and for the reference image. In a further step, this value is compared to each portion. The comparison can be made in different ways. A difference value or a ratio (quotient) of the representative color- or grey value for the scanned digital image and the representative color- or grey value for the reference image may be calculated. It is also possible to enter the color values into a color circle and to determine the angular difference. The compare value determined in such a way will serve for the further processing of the scanned digital image.

A compare value can be determined from a correction value to correct the scanned digital image. Only small defects are visualized on the image in such a way, while large defects are corrected. However, it is also possible to only image the compare value or correction value. Then, only large-area defects are visualized.

With the method according to the present invention it was recognized that the inspected defects are local variations. Large variations of the color or of the brightness can be accounted for by a suitable choice of the size of the portions and will therefore not be considered during the inspection of local defects. On the other hand, large variations can be additionally visualized and/or detected.

The reference image can be generated in any suitable way. It is possible to use the golden image of a wafer which is as perfect as possible. However, it is also possible to use a reference image which is generated of a plurality of pre-reference images previously scanned. The reference images may be generated by averaging several pre-reference images of wafers used for the generation of the references. Values representing color- or grey values for each portion scanned from such reference images form a set of representative color- or grey values for the wafer without the possibly present variation of the color- or grey values along the wafer. The comparison of the representative color- or grey values to the color- or grey values of the portions provides the variation of the actually scanned digital image of the wafer from the image of the reference wafer and values for color changes over the wafer.

In a further modification of the invention a color map is generated in addition to the set of representative color- or grey values for the reference wafer determined in such a way. With such a color map the variation of all considered portions of this wafer can be determined. The result may be used as a reference color map. Only the variation regarding this reference color map is shown when evaluating the images of the inspected wafers.

In an alternative modification of the invention the reference images can be generated from a data base with wafer data. The reference images may also be obtained from a local comparison with the scanned wafer itself.

The generation of reference images on the inspected wafer itself by using adjacent local positions has the advantage that the main portion of the color variation is already eliminated by the generation of the reference image. Thereby, suppression of the color variation is facilitated. A determination and illustration of the global color trend of the wafer is not carried out. This cannot be determined easily with simple means from the image data.

The use of reference positions distributed over the entire wafer will reduce the advantage of elimination of color variations with the generation of a reference. However, the full information content regarding large-area color variations is not even then accessible. This is due to the fact that the color variation of the image of the reference wafer is still not detected.

Preferably, the correction value determined in step (f) is set to be a factor 1 if the determined correction value is outside a selected portion. In other words: if the correction value exceeds a threshold, the original value remains uncorrected. In this case a defect is present.

In some applications of the invention it is useful if a uniform color- or grey value is attributed to selected portions of the scanned digital image and of the reference image.

The reference image and the scanned digital images are quasi masked before further processing. Ranges which shall not be inspected or which commonly cause a false detection are masked. Such ranges are, for example, scribelines between the dies on a semiconductor wafer. The uniform color- or grey value can be, for example, the value 0.

Preferably, the size of the portions is selected such that the compare values of adjacent portions vary less with one from the other than a selected threshold value. The size of the portions is the grid for detecting defects. Large variations are detected with large portions while small defects are averaged. With smaller portions more small defects are suppressed by the correction. With the selection of the size of the portions, the grid for the determination of defects can be selected.

The size of the portions is selected in such a way that the normally occurring large-area color variations on the wafer will not cause a considerable gradient of the color values within a portion. Therefore, the representative color values within a portion vary only within a certain range. The size is selected in such a way that the structure of the wafers is sufficiently averaged. With this choice of the size of the portions, the variations between the scanned digital image of a wafer and the reference image and the variations within the scanned digital image can be eliminated by the comparison with the reference described above. Simultaneously, the representative color- or grey values of the portions can be used for the generation of an overall illustration of the color variation of the wafer.

The color variation image serves to visualize two important effects: the large-area color variation over the wafer caused by, for example, radial layer thickness variations of resist or oxides and the occurrence of local, color inhomogenities in the lateral order of magnitude of the size of the portions, such as, for example, so called comets or fine flowmarks.

Both effects provide particular challenges for the inspection methods as the size is generally considerably larger than the lateral resolution limit of available macro inspection systems, but they are difficult to recognize due to their very small contrast to the environment or the reference.

The determination of a suitable size of the portions can be carried out manually by empiric experiments. Alternatively, the determination can be automatically carried out by the image processing algorithms.

In case of an automatic determination a complete image of the reference wafer can be scanned. The image can then be compressed to a color variation image. For this purpose the representative average color values are determined in a first grid with a first size of the portions without comparison to a reference. The first grid must be finer than the expected size of the portions. The optimum size of the portions is obtained from this first color variation image in that the size is determined, where the difference of the color values of two adjacent portions just does not exceed a set threshold value.

For finding this size of the portions one can simply start with the first size. Subsequently, the variations are checked regarding the selected threshold value. If the threshold is not exceeded, the size of the portions is enlarged by a factor. The factor may be, for example, 2. The iteration method is repeated until the threshold is exceeded.

Preferably, instead of using a set factor generally known search methods are used for the optimum design of the search algorithm. Such search algorithms are, for example, bisectional search, hunt or combinations thereof. The search methods enable the adaptation of the step width until the next size to be tested using the search history. Thereby the accuracy of the determined size can be improved as it is well known and the time consumption of the search process can be simultaneously minimized.

In a preferred modification of the invention, the size of the portions is adapted to the variations over the scanned digital image, wherein the size of the portions in ranges with large variations is smaller than the size of the portions in ranges with small variations. The size of the portions along the wafer are adapted to the dependence of the average color values. In ranges with large gradients of the color values, the size is reduced in order to better follow the changes of the color values. In ranges with small gradients, larger portions may be used to save computing time. Often radial symmetric color profiles occur on wafers where the adaptation of the sizes of the portions can be reduced to a radial gradation.

Alternatively, the variation of the average values of the color value can be regarded separately for the reference- and the scanned digital image. A suitable size of a portion will result from the fact that the values of adjacent portions in both images differ no more than a threshold.

In the most simple case a minimum size of the portions forms the basis for the adaption. All further, larger sizes are generated by a multiplication of the basic size in x- and y-direction with an integer. It is, however, also possible to change the sizes more flexible.

In a further modification of the invention the portions overlap. Such an overlap does not do any harm to the detection and illustration of color defects but promotes the better adaptation of the visualization to the reality. It must only be considered if additional, especially statistic statements shall be obtained from the color variation values.

Alternatively, instead of using a grid of portions it is possible to do the described color background determination individually for each point by using the well known sliding window technique. This means that for each point the color background is determined from a surrounding window area. The size of this area may be the size of above discussed portions. Also one can choose a larger window area since a weight function can be used for the window, determining the influence of each window point to the (central) point under consideration. Usually, those weight functions would have Gaussian, sin-square or similar characteristics making the influence smaller the farer the window point is away from the central point. Using a sliding window instead of a portion grid has the advantage of a smoother result, but suffers slightly from higher computational effort.

The method is suitable for repeating structures of dies on a wafer as well as if uniform, unstructured samples are investigated, such as, for example, blank wafers or wafers with homogenous test- or examination layers.

Additionally to or instead of correcting each image of the scanned digital image with a correction value, the correction value itself may be provided instead of the image point. The visualization of the correction value enables an overview if and to what extent the colors vary over the entire wafer. In particular, variations of such correction values may be spread, i.e., only values in a certain range are displayed, where the values actually change. The dependence can then be better seen in such a way. The magnification of the color variations can be linear or by using a factor. Depending on the algorithm the correction can be the compare value or its reciprocal value.

Steps (c) to (f) may be repeated with a different size of the portions. A smaller size for the portions will lead to a finer correction.

The correction of the images and the illustration of the compare- and/or correction values enables the output of statistic values. Such statistic values can comprise the maximum and the minimum of the color values and differences. The statistic values can be used for signaling the exceeding or falling below a threshold value.

Furthermore, the compare- and/or correction values can be used for calibration of color values or difference values to process parameters. Such process parameters are, for example, the layer thickness, the structure width or their variations.

Further modifications of the invention are subject matter of the subclaims. An embodiment is described below in greater detail with reference to the accompanying drawings.

BRIEF DESCRIPTION OF THE DRAWINGS

FIGS. 1a-d illustrate the portions of a wafer for inspection.
FIGS. 2a-b illustrate the dependence of the correction value.

DESCRIPTION OF THE EMBODIMENT

FIG. 1 shows a wafer generally denoted with numeral 10. The wafer 10 has defects 12, 14, 16, and 18. Furthermore, the wafer 10 has production caused color variations which are illustrated by a shadow 20 with different grey values.

The wafer 10 is inspected with an ordinary inspection device. The image of the entire wafer is scanned. Each image consists of a plurality of image points. In the present embodiment three color channels red, green and blue are attributed to each image point. This color space is also called RGB. An intensity value is measured for each image point in each color channel. This is the color value. In other words: Three color values are related to each image point which are in the present embodiment between 0=no intensity and 255=maximum brightness. Unwanted ranges are masked by attributing the value 0.

The image scanned of the wafer 10 is divided into portions by means of a grid. By way of example, a portion 24 is marked by a bold line in FIG. 1a. FIGS. 1b to 1d each show one portion. Obviously, the representations in FIG. 1 are for illustration purposes only and are not drafted to scale.

In a first step the color values of a portion 24 in each color channel are averaged resulting in a value $MSI_{ch}$. For each channel there are as many representative color values as there are portions.

For the recognition of defects, reference images are generated with known inspection devices. A reference image is an image of a wafer without defects and can be obtained in various ways. The reference image used in this embodiment is also divided in the same portions. Representative color values are determined also for the reference image by forming the arithmetic average value $MRI_{ch}$. In the present embodiment the representative color values are the arithmetic average value of all color values of a portion in the respective color channel. In an alternative embodiment the median value is used.

FIG. 1b shows a portion of the reference image. FIG. 1c shows the same portion, but of the image scanned for inspection.

Subsequently, the quotient $F_{ch}$ is calculated of the average value of the reference image $MRI_{ch}$ and the average value of the scanned digital image $MSI_{ch}$ for each portion and for each color channel. This quotient constitutes the compare value. The result $MRI_{ch}/MSI_{ch}=F_{ch}$ of the calculated quotient is compared to a threshold $M_{Th}$. Varying values are omitted.

FIG. 1d shows the portion of FIG. 1c after the values on all image points have been corrected with the correction value. It can be seen, that the color variations were fully corrected.

FIG. 2 illustrates the correction value in each of the portions 24. It can be seen that the correction value follows the distribution of the color values. FIG. 2b shows the dependence of the color values along a line 26 through wafer 10.

Alternatively, the subsequent correction can be carried out for each portion independently from the value of the compare value $F_{ch}$, i.e. without comparison to the threshold value $M_{Th}$. All pixel values, i.e. RGB-values of the respective portions in the scanned digital image are multiplied with the compare value $F_{ch}$ in order to transform the average color of the scanned portion to the average color of the same portion in the reference image. For this purpose the respective color value is multiplied with the compare value $F_{ch}$ for each image point of each portion in each channel.

The factor for the adaptation of the color values in the corrected image CoScIm is, therefore, the product $F_{ch}$*ScIm of the compare value $F_{ch}$ and the scanned value ScIm on the image point for each image point and each color channel. The corrected scanned digital image CoScIm can then be further processed with defect recognition routines in order to recognize the defects 12, 14, 16 and 18 as the difference between the scanned digital image and the corresponding reference image. Due to the correction carried out previously, it can be operated with much higher sensitivity than without such a correction. Much smaller threshold values can be used for the difference from the image point as being varying, i.e. defect. In other words: The correction has eliminated the allowed large-area color variations while the defects are maintained.

In a further embodiment of the invention a conversion of the color space is carried out before the evaluation of the colors.

It is advantageous to transform the image into a color space for further evaluation where the color is expressed by only one color value as in the RGB color space the color is described by three values, i.e. red-, green- and blue portion, which must be combined. Such a color space is, for example, the HSV-space the color is expressed by hue, saturation and value. In this embodiment the correction follows the same scheme.

After the transformation of the scanned and reference images into the HSV-space they are again divided into portions. A representative hue value is determined for each portion in the form of the arithmetic average value of all hue values of a portion. In an alternative embodiment the median value is used. The same calculation is carried out for the saturation and the value. This results in three values $MSI_{ch}$ and $MRI_{ch}$ for each channel (hue, saturation, value).

Using a HSV space it is advantageous to determine the correction value $F_{hue}$ for the color channel from the difference between the hue value of the reference portion and the average hue value of the scanned portion. The scanned digital image is then corrected to be the image for processing according to CoScIm=$F_{hue}$+ScIm for each image point.

Generally, it is sufficient in the HSV space to correct with the hue value. A better result is obtained if the two other values (saturation and value) are also corrected. For this a quotient is used as correction value. All HSV-values of image points of a portion are corrected in the scanned digital image according to the method described above.

In both embodiments the determined correction values themselves may be assembled to an overall image of the inspected object and visualized. The overall image provides an overview over the colors and enables to find large defects and variations. Such large defects and variations will not show up as local, small area defects but in the form of large areas. They are comparable with the size of the portions up to the size of the entire sample. In particular, variations can be found where the variation in the individual RGB- or HSV-values of the image points with respect to the reference sample are very small. With a suitable scaling the image with the overview over the colors can be adapted to the individual object of the inspection. If it is interesting to know, if the actual scan wafer varies in color from the reference with large areas or even with the entire area, a fixed scale can be used for the wafer kind. Thereby, trends and variations of the color can be well monitored. If it is interesting to know about local variations the scale of the determined color correction values is spread as wide as possible. If, for example, the determination of the color correction for the entire wafer results in values between 13 and 21 and if the representation is possible with 255 steps, a scaled value y can be determined from the correction value x according to $$y = 255 * \frac{x-13}{21-13}$$

and be displayed as y-values using the entire range between 0 and 255. Obviously, both scales can be applied parallel on copies of the images or successively in order to optimally fulfill both inspection purposes.

The above description was given for a better understanding by way of example using precise numbers and values regarding the amount of image points, the size of the portions and the formation of average values and threshold values. It is understood that there are only two embodiments of a great number of embodiments of this invention are described. The invention may well be used with different sizes of the portions etc.

What is claimed is:

1. Method for inspecting flat objects, especially wafers, with an object surface, the method comprising the steps of:
    (a) scanning a digital image with a plurality of image points of said object surface with color- or grey values for each of said image points;
    (b) detecting defects on said object surface by comparing said scanned digital image to a digital reference image;
    (c) defining and selecting corresponding portions in said scanned digital image and in the digital reference image;
    (d) determining a representative color- or grey value for each of said selected portions;
    (e) calculating a compare value from said representative color- or grey value of said scanned digital image of a portion and a representative color- or grey value of said digital reference image of the same portion;
    (f) correcting each image point of said scanned digital image with a correction value determined from said compare value of step (e); and
    (g) wherein the size of said portions is selected such that said compare values of adjacent portions vary less with one from the other than a selected threshold value.

2. A method according to claim 1, and wherein said representative color- or grey value is an arithmetic average value or a median value of said color- or grey values for said image points in said selected portion.

3. A method according to claim 1, and wherein said correction value is a ratio (quotient) or a difference of said representative color- or grey value for said scanned digital image and said representative color- or grey value for said digital reference image.

4. A method according to claim 1, and wherein said correction value determined according to step (f) is set to be factor 1, if the determined correction value exceeds a threshold.

5. A method according to claim 1, and wherein a uniform color- or grey value is attributed to selected portions of said scanned digital image and of said digital reference image.

6. A method according to claim 1, and wherein said threshold value is selected such that the structure of the object surface is just not resolved anymore and large color variations over said object surface do not cause recognizable gradient of said color values within a portion.

7. A method according to claim 1, and wherein the size of said portions is adapted to variations in said compare values over said scanned digital image, wherein the size of said portions in ranges with large variations is smaller than the size of said portions in ranges with small variations.

8. A method according to claim 1, and wherein the size of said portions is determined by iteration until differences in the said compare values of two adjacent portions is just within a selected range.

9. A method according to claim 1, and wherein said portions overlap.

10. A method according to claim 1, and wherein additionally to or instead of correcting each image point of said scanned digital image with a correction value said correction value itself is provided at each image point instead of said image point value.

11. A method according to claim 1, and wherein steps (c) to (f) are repeated with a different size of said portions.

12. A method according to claim 1, and Wherein said correction value is determined for each point individually by using a window around said point.

* * * * *